United States Patent [19]

Sheehy

[11] Patent Number: 5,527,712

[45] Date of Patent: Jun. 18, 1996

[54] SUBSTRATE AND PROCESS FOR FORMING SUBSTRATE FOR SURFACE-ENHANCED ANALYTICAL PROCEDURES

[75] Inventor: Timothy M. Sheehy, Las Vegas, Nev.

[73] Assignee: Medifor Limited, an Irish Corporation, Geneva, Switzerland

[21] Appl. No.: 453,443

[22] Filed: May 30, 1995

Related U.S. Application Data

[63] Continuation of Ser. No. 138,890, Oct. 19, 1993, abandoned, which is a continuation of Ser. No. 858,163, Mar. 27, 1992, abandoned, which is a continuation-in-part of Ser. No. 733,728, Jul. 22, 1991, abandoned.

[51] Int. Cl.$^6$ ................................................. G01N 33/553
[52] U.S. Cl. .................. 436/525; 427/287; 427/383.1; 427/404; 427/414; 422/57; 422/58; 436/518; 436/527; 436/531; 436/532; 436/534; 436/805
[58] Field of Search ................................ 427/287, 383.1, 427/404, 414; 422/55, 57, 58, 82.05, 82.08; 436/172, 518, 525, 527, 531, 532, 534, 805

[56] References Cited

U.S. PATENT DOCUMENTS

| | | | |
|---|---|---|---|
| 4,267,234 | 5/1981 | Rembaum | 428/407 |
| 4,267,235 | 5/1981 | Rembaum et al. | 428/407 |
| 4,369,226 | 1/1983 | Rembaum | 436/531 |
| 4,438,239 | 3/1984 | Rembaum et al. | 435/7.1 |
| 4,978,503 | 12/1990 | Shanks et al. | 422/82.11 |
| 4,992,385 | 2/1991 | Godfrey | 422/82.11 |

OTHER PUBLICATIONS

D. A. Weitz et al, J. Electron Spectroscopy and Related Phenomena, 29 (1983), p. 363, A Comparison of Raman Scattering, Resonance Raman Scattering, and Flourescence from Molecules, absorbed on Silver Island Films.

T. M. Cotton et al, J. Physical Chemistry, 1986, 90–6071–6073 Distance Dependence of Surface–Enhanced Resonance Raman Enhancement in Langmuir–Blodgett Dye Multilayers.

Thomas E. Rohr et al, Analytical Biochemistry (1989), p. 182, Avidin–Coated Silver Films Demonstrated SERS with Antigen–Antibdy reactions. Antibody coated Directly on the Surface.

Dellerich, "Enzyme–Immunoassay: A Review", J. Clin. Chem. Clin. Biochem., vol. 22, 1984, pp. 895–904.

*Primary Examiner*—James C. Housel
*Assistant Examiner*—Christopher L. Chin
*Attorney, Agent, or Firm*—Sherman & Sherman; Kenneth L. Sherman

[57] ABSTRACT

A substrate for surface-enhanced analytical procedures, such substrates prepared for use in specific procedures to detect specific binding partner molecules, and a method for making them. The substrate is a body having a substrate surface on which there are randomly spaced apart metal islands. A continuous layer of coupling agent coats the islands and any intervening substrate surface. First binding partner molecules are bonded to the coupling agent. These are specifically attractive to specified second partner molecules for an analytical procedure for detecting the presence of, and perhaps the concentration of second partner molecules, or in some procedures, of a specified third binding partner molecule which becomes bonded to the second binding partner molecule. The thickness of the coupling agent layer is selected to improve the sensitivity of a given analytical procedure for detecting or measuring the specific binding partner molecule.

26 Claims, 2 Drawing Sheets

SUBSTRATE AND PROCESS FOR FORMING SUBSTRATE FOR SURFACE-ENHANCED ANALYTICAL PROCEDURES

CROSS REFERENCE TO OTHER PATENT APPLICATION

This is a continuation of application Ser. No. 08/138,890, filed on Oct. 19, 1993, for a SUBSTRATE FOR SURFACE-ENHANCED ANALYTICAL PROCEDURES, now abandoned, which is a continuation of applicant's U.S. patent application Ser. No. 07/858,163 filed Mar. 27, 1992, now abandoned, which in turn was a continuation-in-part of U.S. patent application Ser. No. 07/733,728, filed Jul. 24, 1991, also now abandoned.

FIELD OF THE INVENTION

Although the term "immunoassay" is most commonly used for analytical techniques in which an antigen and antibody response is measured in order to determine the presence and concentration of one of them, in fact it is a special case of a more generic technique in which two "partners" provide a measurable response. In many such situations substances which are neither an antigen nor an antibody provide responses analogous to those of an antigen-antibody system. These, as well as antigens and antibodies, are partner-specific in the sense that in the correct environment they bind only to each other, and the extent to which this binding occurs is the basis for analytical procedures. Because immunoassays are the most widely used procedures of this type, they will be described in more detail than the others. However, when the term "immunoassay" is used herein, it will be recognized as being descriptive also of surface-enhanced chemical analyses generally, which utilize partner-specific combinations.

This invention relates to surface-enhanced chemical analysis procedures, and to consumables used in these procedures.

BACKGROUND OF THE INVENTION

Quantitative analyses sensitive to extremely low concentrations are regularly made with immunoassay techniques. The term "immunoassay" is generic to a wide variety of processes and procedures. Basically it involves a partner-specific interaction of a plurality of partner substances which are preferentially attracted to one another. A well-known example is an antibody of known specificity which is one of the partners and is to be receptive of an antigen (the other of the partners). The presence and concentration of one of them is to be detected and measured in the immunoassay procedure. As stated above, immunoassays are examples of techniques useful in other than antibody/antigen situations, as will later be discussed.

There are two basic analytical techniques, the "sandwich" technique and the "competitive" technique. Both of these techniques are widely used, and in each of them the amount of the partners bonded together is either directly measured, or is measured by way of difference. Persons skilled in this art are already fully aware of these techniques, and these techniques per se are not the instant invention.

It has long been recognized that an immunoassay is a sensitive procedure and is at least theoretically able to perform assays beyond the abilities of even the most sensitive of other known procedures. However, its processes have been very slow and inconvenient to use, sensitivity has been variable and often low, and repeatability has been well below what the process theoretically should be able to deliver. Also the consumables required for these procedures have had short shelf lives and have required more attention to their use than is desirable in what should be a highly automated and speedy procedure. This is also true of other than antibody/antigen situations.

Not surprisingly, considerable efforts have been made in the past decade to reduce surface-based analytical processes to a convenient laboratory analysis procedure. Especially strong efforts have been made in surface enhancement. Some efforts at surface enhancement have produced significant improvements, but these have been unaccompanied by suitable explanations or understandings of how these improvements occur, or for that matter, even what they are. Instead the art has developed pragmatically, step-by-step, and by now the dangers of trying definitely to explain the rationale of them have become very apparent. The newer procedures either work better, or they do not.

As it happens, tremendous increases in sensitivity can be attained with the use of any of the three best-known techniques of surface enhancement. One is surface enhanced fluorescence, another is surface enhanced Raman spectroscopy, and the other is surface enhanced colorimetric procedures. This invention improves the sensitivity, accuracy, convenience, speed and availability of all of these procedures, and provides the basis for a very effective consumable for use in these procedures.

These procedures all require the adherence of a specific partner or partners to a surface. Both planar and spherical substrates are known in the art. One means for enhancing adhesion of the partner to the substrate is to coat the surface of the substrate with a coupling agent which is adherent to the surface, and this technique is known. This invention also serves that function. Importantly, it also serves as a means accurately to space the partner from a metal-laden substrate surface, the accuracy of which spacing profoundly increases the sensitivity of the procedure, which is not, a previously known fact. Further, it also protects the partners from deleterious reactions with metals that may be placed on the substrate.

Polyglutaraldehyde ("PGA" herein) is a preferred coupling agent. A suitably prepared surface coated with PGA (or with any other suitable coupling agent) will in fact reliably retain a substantially greater amount of a partner to its surface than would be retained by a substrate surface which is not coated with such a coupling agent. This is another feature which increases the sensitivity of the procedure.

The enhanced retention of a partner by the coupling agent along with the accuracy of spacing provided by a carefully controlled thickness of coupling agent constitutes a basis for a multiplied effectiveness of the procedures.

Procedures according to this invention are a wet process. They depend on the kinetics of contact between the partner on the layer of coupling agent and the patient sample which includes the other partner. The patient sample is characteristically diluted in a buffer solution. As in all contact processes, the gross rate at which the reaction occurs is a function (among other variables) of the total surface area to be contacted, and of the transfer distance the molecules must travel or transfer to reach the PGA layer.

A method for increasing the gross rate is to increase the surface area, and to agitate the reactants to increase the likelihood of access of the partner molecules to the partner on the coupling agent layer. This is a worthwhile approach within the scope of this invention, but requires a substantial amount of buffer solution. For many immunoassay procedures this is a viable alternative. However, in many other, the cost of the buffered solution which often includes an expensive partner in wasteful amounts is extraordinarily high, and can render the procedure uneconomical. Such circumstances can exist, for example, when the buffer solution must include as a partner a clonal protein whose cost is very high.

Still, when a large increase in surface area is useful and buffer costs are affordable, a large number of small bodies such as microspheres coated with the coupling agent will advantageously be utilized. Microspheres or other very small bodies coated with a coupling agent such as PGA will retain many times the amount of partner that would be retained by even a very large number of planar surfaces such as glass slides. This is because of the very large increase in surface area of an increased number of very small bodies, especially of spheres. A principal advantage of these small substrates is that in a substantial body of liquid they enable the assay process to proceed at rates which approach those defined by solution kinetics. This contrasts with kinetics applicable for reactions at a fixed surface such as a glass plate where transfer of molecules to the PGA surface is inherently very slow.

However, and rather surprisingly, with this invention a flat plate can be utilized to provide reaction speeds approaching those of solution kinetics using microspheres, and with a large reduction in the requirement for a buffering solution. This is accomplished with the use of reaction regions of capillary dimensions, such that the partner in the buffering solution is very closely situated relative to the partner on the binding agent and are subject to capillary forces, so closely and uniformly that even without agitation the speed of the reaction approaches that which occurs in a well-stirred solution.

Another observation has been made that very small metallic metal islands (silver, for example) on a substrate to which a partner is directly adherent can result in substantial enhancement of sensitivity of the surface-enhanced analytical process. This has previously been accomplished with silver islands on flat glass plates. Here it may be observed that a smooth continuous plating of metallic silver does not produce much improvement in sensitivity, but that a toughened surface does produce at least improvement over that obtainable with the use of a smooth silver surface, although still much less than of separate islands. The reasons for all of this still reside in the realm of speculation, but it is observable that silver islands separate from one another produce a greatly improved assay, and that a suitably toughened one gives at least some improvement. As will later be disclosed, silver is only one example of a suitable metal for this purpose.

A problem solved by this invention resides in the distance-dependency of a partner from the metal islands. For fluoroscopic techniques a relatively large spacing provides best enhancement, while for Raman spectroscopy techniques, a smaller spacing provides best enhancement. In both cases there is an optimum spacing, and deviation from it results in less enhancement Accordingly, in this invention, the coupling agent has a function in addition to its capacity to bind a partner—it is to provide a very accurate spacing of its exposed surface from the substrate (including the islands) in order to improve the sensitivity of the procedure.

Whatever the situation, the art as presently known does not provide a convenient source of a known amount of partner compound for a suitably rapid analysis procedure. All surface-enhanced analytical procedures require a "consumable" which must be provided at the outset of each assay procedure. It is an object of this invention to provide a convenient consumable of known and optimized properties and good shelf life, thereby greatly improving the convenience and reliability of analyses utilizing the partners involved.

In fact, analyses using this invention are more sensitive by at least several degrees of magnitude compared to analogous analytical procedures, and complete their reactions between about 8 and 20 times faster than other known procedures. The repeatability of the procedure is greatly improved, and the analytical procedure can be simplified.

This invention provides a remarkably improved analytical procedure, and a consumable (sometimes called a "surfaced article") for accomplishing it.

BRIEF DESCRIPTION OF THE INVENTION

This invention comprehends the use of a substrate which bears metal islands with which a partner is physically and spatially related. As in any immunoassay procedure, the assay depends for its response on the extent to which one partner becomes attached to another partner. For any assay of this type, a particular partner (often but not always a protein) is attached by some means to a substrate of some kind. Thereafter, in the course of the assay, another partner which is to be detected and/or measured, contacts the partner on the substrate (sometimes through an intermediate). By one means or another, the occurrence and perhaps the extent of the binding reaction between a binding reaction occurs. Then a measurement can be made to determine the presence, and usually also the concentration of the other partner.

According to this invention the substrate is first at least partially surfaced with metal islands. These islands are preferably somewhat circular or disc-like, having a very small thickness. As viewed microscopically, they preferably constitute a discontinuous metal layer. To the extent that smaller islands meet or coalesce, the benefits of this invention are significantly reduced. The preferred embodiment has a substrate which is partially coated with very small and very thin metal islands, separated from one another.

However, and rather surprisingly, a suitably toughened continuous metal surface provides at least some improvement. It appears that the "peaks" of its roughness tend to provide structure which at least simulates the properties of isolated islands. For this reason, the "peaks" of a suitably roughened metal surface are also called "islands", and are within the scope of this invention. In fact, this effect occurs on the surface of suitably rough metal bodies.

Atop the base surface comprising the islands and any uncoated substrate (where and if it occurs) is a continuous layer of a coupling agent, for example PGA. The thickness of this layer is established by the parameters of the process to be employed for making it, but will be known and accurately formed. The layer, of any useful thickness, will provide for attachment of a larger amount of partner than would be bonded to an uncoated surface, which is a feature of the coupling agent. In fact it is this larger area of effective surface for partner attachment that in part provides an improved response because of the larger amounts of partner available to the process, and because of the more uniform concentration of the partner which is retained on unit surface areas of the surfaced article. This enables a much closer control over the parameters of the process. The controlled thickness of the coupling agent layer also contributes to the function of a distance dependent relationship to the degree of enhancement, because surface enhancement is dependent to a surprising degree on the spacing of the partner from the metal islands on the substrate. The coupling agent also protects the partner from adverse reaction with the metal.

According to this invention, the area and thickness of the metal islands and the thickness of the coupling agent coating are mutually related relative to the partner to be bonded to the coated substrate so as to respond most effectively to the radiation or to the response caused by the radiation, the response constituting the recognition of the presence of, or the concentration of, the other partner. The physical parameters employed depend on the type of assay (fluorescent, Raman, or colorimetric).

The above and other features of this invention will be fully understood from the following detailed description and the accompanying drawings, in which:

DETAILED DESCRIPTION OF THE INVENTION

Figure 1:
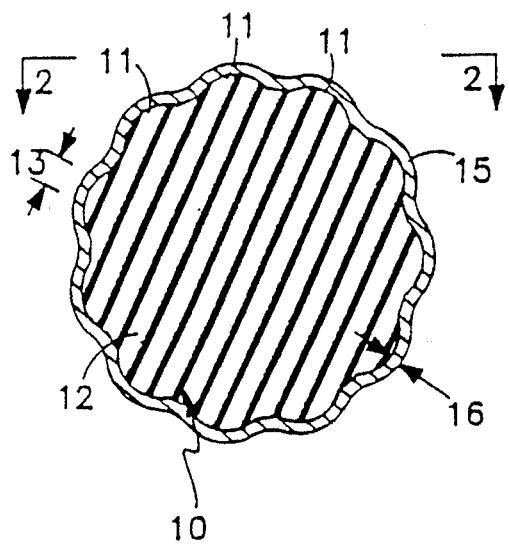
FIG. 1 is a cross section of the presently-preferred embodiment of a surfaced article according to this invention.

FIG. 1 shows a cross-section of a microsphere 10 with a plurality of metallic islands 11 on its surface 12. The islands have a nominal lateral dimension 13 which can conveniently be thought of as the diameter of a circular disk, although it is evident that these extremely small islands will not usually be true circles, nor is there any known reason why they should be. Each has a nominal thickness 16. The nominal diameter and the thickness of the islands will be discussed later in this specification. A layer 15 of coupling agent yet to be described is laid over the islands and over substrate body surfaces between the islands.

Figure 3:
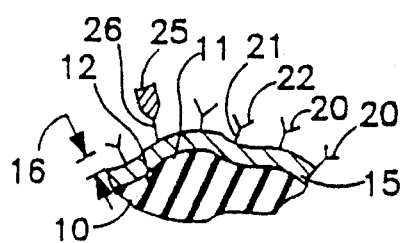
FIG. 3 is a fragmentary portion of FIG. 1, enlarged and utilizing a schematic notation.

FIG. 3 is necessarily schematic. It is intended to illustrate a portion of the surface of a coupling agent-coated microsphere 10 which has been contacted by a solution containing a first partner 20. Very often this partner will be an antibody. The partner is bonded or somehow attached to the coupling agent. It is schematically shown as having a stem 21 and a branched receptor 22, which is a conventional schematic representation. The stem is bonded to the coupling agent by means not fully understood, and the receptor in actuality has a structure unique to the portion of a second partner whose presence and also perhaps its concentration are to be detected and measured, because the two partners through the receptor have a unique relationship to one another.

The theory of the assay is that a second partner 25 has a moiety 26 which "matches" receptor 22, and is captured in it. This simplistic explanation is not rigorous, but it does serve to explain the function of the consumable which bears the first partner.

The first partner is selected to be uniquely receptive to a specific second partner. When the microspheres are placed in a liquid medium that includes the second partner to be detected or measured, it seeks out the first partner on the microsphere. Thereafter the presence and concentration second partner can be sensed or measured by known techniques. As will later be described, in some procedures, the partner to be bonded to the first partner may not be the substance whose presence or concentration is the subject of the procedure. In some procedures, that substance may not bond directly to the first partner. Instead, it might be a third partner which bonds to the second partner. The second partners all bond to the first partner, and the presence and perhaps the amount of the third partner that is bonded in this manner becomes the subject of investigation.

As will later be disclosed, a myriad of the above described, coated microspheres can be used in a liquid suspension to provide a very large reactive surface area as a function of their shape and large numbers. Further, because of their small size, they will tend to remain in suspension without major settling-out for a sufficient and considerable time. This time generally will approach four hours, while the longest procedure will usually require only about one hour. This is the basis for the statement that the response of the process using microspheres is quite near to that of a true fluid kinetics procedure.

Of course, spheres are not the only useful shape, although they are the most easily made with closely controlled dimensions. Other shapes may also be used, bearing in mind the multiplication of total surface area which occurs when a larger body is reduced to a larger number of much smaller bodies. Irregular bodies, or regular bodies of various shapes such as cubes and other polyhedrons can also be used, but are much more difficult to make. All can be suitably coated with metal islands and coupling agent.

Large flat plates have long been used for immunoassays. Plates bearing only silver islands or only coupling agents are known for this purpose, but not in combination to the present knowledge of the inventor herein. The sensitivity of the reaction in the absence of the combination of islands and controlled thickness of coupling agent of this invention is so reduced as to render the process economically non-competitive except in those few instances where there is no viable alternative. The root of the problem is the slow reaction due to the stagnancy of the fluid near the contact surface, the relatively small total area of the surface, and the relatively small amount of partner which will reliably be retained on an uncoated metal surface.

With this invention, not only can there be surface enhancement on a large flat plate, but by taking advantage of capillary phenomena, a reaction speed can be attained which approaches that which can be attained with classic fluid kinetics. Furthermore, the volume of buffer solution, which can be very expensive, can be reduced to a bare minimum. In the medical testing field, one test will sell in preference to another when the costs differ even in fractions of cents, and when speeds of the tests differ even in seconds.

Figure 5:
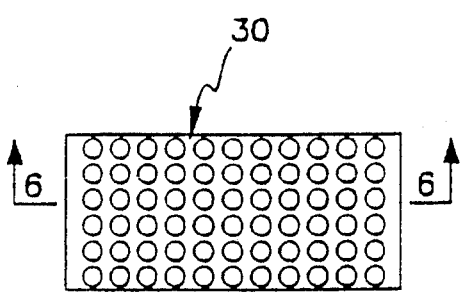
FIG. 5 is a plan view of another embodiment of a surfaced article.
Figure 6:
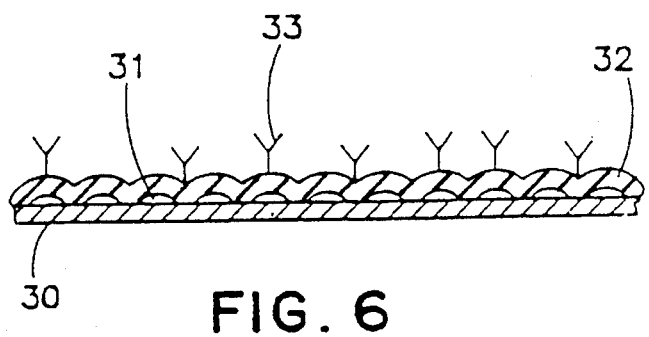
FIG. 6 is a cross-section taken at line 6—6 in FIG. 5.
Figure 7:
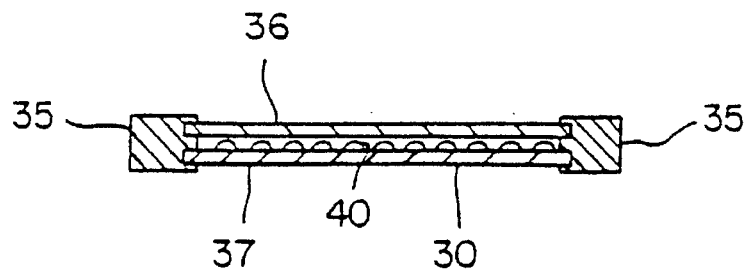
FIG. 7 is a cross-section of a device using the article of FIG. 5 taken at line 7—7 in FIG. 8.

For this purpose, as shown in FIGS. 5 and 6, a very flat substrate plate 30, usually of glass, has metal islands 31 as previously described, and a coupling agent layer 32 as previously described. Also, partner 33 is applied to the PGA layer. Now this surface is completely identical to that on the microspheres, except for its shape.

A jig 35 is schematically shown mounting substrate plate 30, and also a cover plate 36. Cover plate 36 is supported by the jig parallel to the substrate plate, and spaced from it by a carefully defined spacing 37.

The size of spacing 37 is determined by the requirement for sufficient buffer solution (including the patient sample) to carry out the test, and to assure a capillary action in the fluid between the plates. The capillary action assures that the buffer solution will spread to cover the entire exposed surface on the substrate plate, and the substances will mix so that no agitation or spreading effort is required.

Furthermore, and of critical importance, is the fact that under these capillary conditions, a thorough mixing of the patient sample and the buffer solution will result, even if they are initially placed between the plates separately.

Even more, the parallelism of the plates and the spreading of the sample-bearing buffer solution results in a thin layer in which transport distance of sample molecules to the coupling agent surface is very short, so that the reaction proceeds swiftly. Had the buffer solution and patient sample simply been dropped on an exposed plate, it would have tended to bead up. Too much solution would be required to cover the plate, and the transport distance would have increased, thereby increasing the cost and slowing the test.

A convenient means to introduce the buffer solution and patient sample between the plates is by means of a thin needle 40 moved in a pattern between the plates while discharging the fluids from a syringe 41. The syringe can conveniently be pre-loaded with a known volume 42 of buffer solution and a known volume 48 of patient sample. They may be separated by a "pig" 44 which is a quantity of air to keep them apart in the syringe. They will mix thoroughly in the capillary space without agitation. The needle is withdrawn after injection, and can be made a disposable item, as can the syringe.

It is convenient for the syringe to be pre-loaded with buffer solution and the pig. The syringe can be a stable pre-loaded article, and then the patient sample is drawn into the syringe just before the test.

Manipulation means (not shown) can be provided to move the tip of the needle into the spacing between the plates, and to insert and withdraw it.

Figure 8:
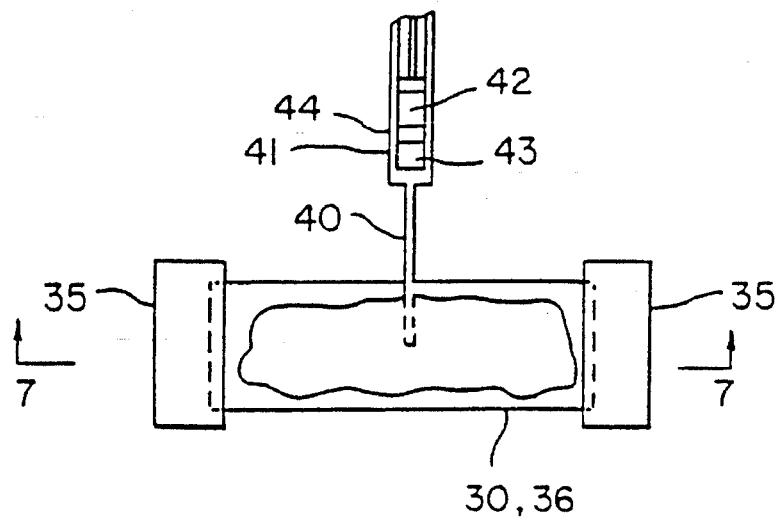
FIG. 8 is a side view of the device of FIG. 7, partly in a cross-section and partly in a schematic notation.
Figure 9:
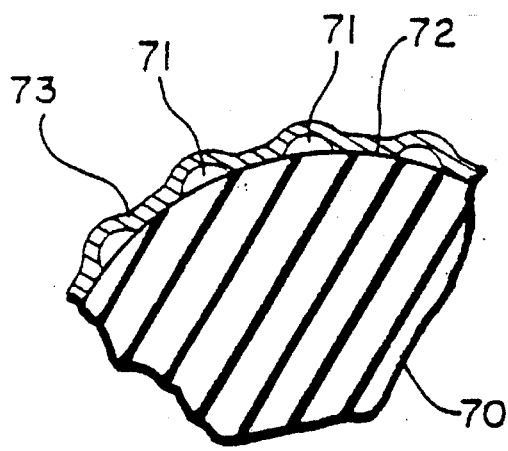
FIG. 9 is a cross-section of another embodiment of the invention.

FIG. 8 shows a rather unusual embodiment of the invention, in which the coupling layer is "imbued" with the first partner. FIG. 9 shows a substrate 70 with a silver islands 71 on its surface 72, according to any of the other examples in this specification. In this embodiment, the coupling agent 78 is a layer, laid on the substrate, which is imbued with the first partner.

A typical example of coupling agent 78 is a slice of tissue in which a first partner (to be detected) is present. Such slices are routinely made by freezing the tissue and slicing it in a microtome while frozen. It is then laid on the substrate, where its thickness corresponds with the built-up thickness of the deposited layers described elsewhere herein.

Because of the cellular and permeable nature of the layer, the first partner will be presented on its exposed surface. There it will behave as though it had been applied as in the other embodiments. Laid layers besides tissue can function in this manner. For example, cellulosic materials, foams and sponges can similarly function. All of these serve to illustrate the fact that the coupling agent need not be impermeable, as PGA is. Instead it need only be retentive to the first partner, which may also imbue the structure of the coupling agent.

Figure 4:
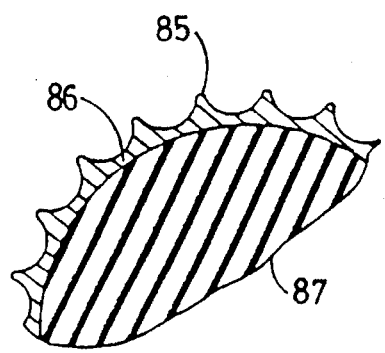
FIG. 4 is a fragment similar to FIG. 1 showing a different arrangement of metal islands.
Figure 10:
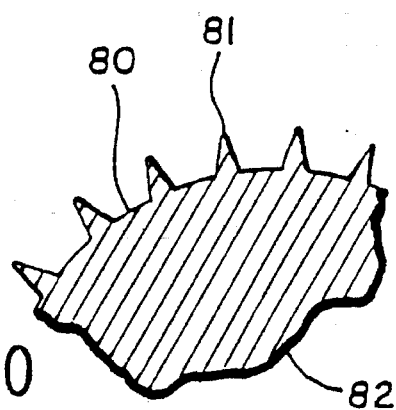
FIG. 10 is a partial cross-section of another embodiment of the invention.

FIG. 10 illustrates that a suitably rough surface 80 with islands 81 on a metal body 82 also function. The surface may resemble that shown in FIG. 4, the difference being in the inner body which in FIG. 10 is metallic. Colloids and sols have suitably rough surfaces, and a silver colloid suspension with its surface coated with a coupling agent layer will provide improved sensitivity. This is not the preferred embodiment, but it does function.

It is an observed fact that different partners, for example proteins bonded to a coupling agent and receptive to another partner protein yield signals of different intensity as a function of thickness of the coupling agent layer, i.e. their spacing from the islands. One can readily theorize why this is so, but that is not the purpose of this specification. Instead, it is intended to disclose thicknesses, and techniques to provide thicknesses, of the coupling agent layer respective to various first partners which position the coupled partner to the metal islands so as to enhance the "signals" which are emitted as the consequence of exposure to selected radiation. The sizes and thicknesses of the PGA coatings, and also of the metal islands, are not susceptible to conventional measurement techniques. Instead for commercial production they are best defined by the processes to make them, and by tests which verify their suitability. Such tests can be accomplished by using them in analytical procedures with known concentrations of partners.

The consumable small bodies such as microspheres or the larger flat plates may at present best be defined by the way they are produced. The following description shows the process to produce an effective product which generally will produce up to about an eight orders of magnitude increase in sensitivity with Raman procedures, and about four orders of magnitude increase with fluorescent and colorimetric procedures. There are other advantages also, such as speed and greater convenience.

The substrate may be made of any suitable non-reactive material to which the metal islands and the coupling-agent can adhere. Polystyrene, glass, latex, polyethylene, nylon, acrylic, polypropylene, silicone rubber, silica and ceramic are all suitable substances. Polystyrene is the most convenient material for small bodies. Glass is preferred for flat plates. Incidentally, any cover plate must be made of a material transparent to the radiation used in the analysis and of its response. Glass is generally not suitable for this. An acrylic will usually be used for a cover plate instead.

Nominal diameters between about 0.1 microns and 10.0 microns for microspheres have been found to give excellent results. When irregular small bodies are used, their lateral dimensions will be in this general range.

There are a number of metals which are useful for the islands. Care will be used in their selection and application. Useful metals can be selected from the group consisting of silver, copper, gold, platinum, nickel, indium and germanium. Some of these are more effective than others, and some are less suitable for some analyses than others because of their possible adverse effects on the protein. For example, gold, platinum, nickel and copper are antagonistic to some antibodies, but not to proteins which are not antibodies. Copper is generally antagonistic to all proteins.

A suitable coupling agent coating can isolate these metals from the first partner and thereby greatly decrease the risk of degradation of the first partner while still permitting the use of that metal, which might provide for good signal enhancement. However, the lesser effectiveness of some of the metals in enhancing the signals strongly supports the use of silver for nearly all procedures. For this reason, silver is used as the illustrative and preferred material in this specification. The process for creating islands of the other metals is similar, differing only in the respective process parameters.

The metal islands can be deposited on the substrate surface with the use of any suitable deposition process. Vapor deposition in a vacuum has proved to be the most advantageous. Of course on microspheres or the like the entire spherical surface may not be coated, because part of it may be shaded, but the population of these islands will be sufficient and generally consistent, so that accuracy of the assay is not adversely affected by the fact that part of the surface does not bear islands.

When isolated islands separated by substrate surface without metal on it are to be formed, care will be taken to avoid completely plating the surface. In the deposition process, islands will initially form, but as the deposition proceeds and the deposited metal becomes thicker, the islands finally collapse and slump to converge into a continuous plating. This ultimate result can be avoided by careful control over the deposition process, and by stopping it immediately when the islands are sufficiently formed. Experience with the process, and adjustment of the timing and conditions of depositions will soon enable the operator to prepare suitable island-coated microspheres (or plates).

The most effective silver islands have a nominal height (thickness) between about 20 angstroms and about 200 Angstroms. Further, as to their size, on a microsphere optimum silver islands will have the following dimensional relationship:

$$\frac{\text{Metal Thickness}}{\text{Nominal diameter + Metal Thickness}} = \text{between about 0.58 and about 0.67}$$

The substrate bodies bearing a layer of small metal islands are next coated with a coupling agent. The ultimately desired thickness of the coupling agent layer for many assays is between 1 Angstrom and about 100 nm, depending on the analytical technique being used, i.e. fluorescent, Raman, or colorimetric A suitable coupling agent can be selected from the group consisting of polyglutaraldehyde (PGA), protein A, protein G, polystyrenes, polyethylenes, polyacrylamides, streptavidin, avidin, and in some procedures slices of tissue or of other porous material of suitable thickness (FIG. 9). All of these will suitably adhere to the exposed surface of the substrate body between the islands, and to the islands themselves. They form a surfacing with a spacing from the islands for reasons to be disclosed, and also when impermeable can form a barrier which isolates the metal islands from the first partner. In addition, and very importantly, the partner will bond to them.

Because PGA is by far the most effective coupling agent, and the easiest with which to form a layer to a controllable thickness, it will be given as the illustrative and preferred embodiment. The other substances may be deposits formed by well-known techniques. The tissue slice will be laid on the surface, but because of its relatively large size, its respective underlying substrate will be a flat plate rather than a microsphere.

PGA is a condensation product from glutaraldehyde. Initial purity of at least 90% monomer is desirable. Before adding the microspheres, an aqueous solution of glutaraldehyde, about 1.5–4.0% is buffered to between about pH 8.0 to pH 11.8, and maintained at a temperature between about 22 degrees C. and 37 degrees C. for between about 30 to 90 minutes. If the pH is lowered, the time will be increased within these limits, and vice versa. It is not intended that polymerization proceed too far in this solution. Instead it is intended for the layer to "grow" on the microspheres.

After sufficient time has elapsed, the microspheres will be added to the solution although if preferred, the microspheres may be added to the aqueous glutaraldehyde earlier. The solution must be maintained on the basic side. pH 10.0 is usually a minimum number pH. The microspheres will be left in the solution for between about 3 to 48 hours, with stirring as necessary to avoid clumping. If the microspheres were added earlier, the elapsed time will be shorter. By this time, a suitable layer of PGA will have been deposited. Later measurements and comparison with the parameters which produced them will with little experimentation find the optimum conditions for making the intended product.

Next the solution is poured off of the microspheres, and they will be washed with a buffered phosphate solution at pH between about 4.0 and 8.0. This will rinse off the unbound-to-surface PGA. Several rinses will be needed, each to be poured off. The product will not be dried.

The cleansed microspheres will now be suspended in an assay buffer, and the first partner respective to an intended future test is added. The first partner will now attach itself to the PGA layer. The entire PGA layer will receive the partner, and retain it stably in quantities greater than the uncoated substrate would have held. The partner which is located over the islands will provide an enhanced signal, as will later be discussed.

After leaving the microspheres in the partner-containing solution for a sufficient period of time at the proper pH and temperature, the solution will be decanted, and the microspheres will be washed several times with a solution of the assay buffer.

If desired, the microspheres can now be treated with a blocking agent. The purpose of the blocking agent is to bind to all unoccupied sites on the PGA surface, that is, sites not already occupied by the first partner. A generally useful blocking agent is BSA (bovine serum albumen) in aqueous solution.

This is the "consumable" sent to the user for use in assays which utilize the first partner carried by the microspheres. Of course a different partner will be provided for assaying different substances, but each is respective to some intended assay.

Consumables using other shapes are formed with the same procedures. Small bodies of sizes comparable to the microspheres are treated just as described above for microspheres. These very small bodies will be completely covered—in fact, encapsulated, by the PGA. They are sometimes referred to as "closed surfaces", because they are continuous, without edges.

Flat plates will receive metal islands as described above, on one side. The PGA layer may thereafter be provided by the entire plate in the solution as described, with a masking on one side if it is desired to coat only one side, or by any other suitable means to isolate and treat only one side of the plate. Of course it is possible to coat both sides, but this will not usually be done. Because the surfaces which are utilized in the procedures have a specifically defined area with edges, they are sometimes referred to as "extended surfaces". They are not closed, and need not be flat and planar, although they most often will be.

Figure 2:
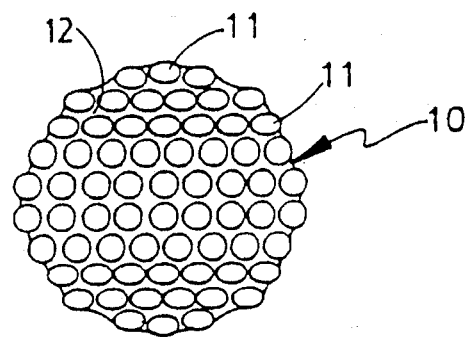
FIG. 2 is a side view taken at line 2—2 in FIG. 1.

If "islands" are to be formed as part of a continuous metal layer that totally covers a substrate, it is necessary to roughen the layer to create them. For example, in FIG. 4, metal islands 85 are shown rising above a metal coating 86 which envelops a plastic substrate body 87, perhaps spherical as in FIGS. 1,2 and 3. This will not be as effective as islands which are more specifically formed as in FIGS. 1–3, but they will still function to improve the sensitivity. To accomplish this, a continuous, uniform metal plating can be first applied to the substrate. Then by ion erosion or otherwise, the metal surface is pitted or otherwise eroded so that some "peaks" of metal rise between "valleys" on the surface. It appears that at least some enhancement is attained with these peaks, and the term "islands" as used herein refers both to those shapes which are spaced apart by metal plating, and those which are spaced apart by unplated substrate material.

For the embodiment of FIG. 10 the treatment is the same as when a non-metal substrate is used except that colloidal particles are generally suitably rough when formed, and often will not require subsequent treatment.

Flat plates and discrete particles in suspension have been described as examples of suitable supports (substrates) for the consumable. However, the coupling agent can be applied to other useful types of supports, for example to the inside of test tubes, to beads in a column, to the wall of a column, to the surface of a foldable bag, to micro-titer plates, strips, and wells, as examples. In these examples, coated particles can be applied to the surfaces, or these various surfaces can be provided with metal islands and then coated with coupling layers. There is no limit to the range of applications.

The procedures for use of the first partner in assay procedures are conventional and known, and require no detailed description here. Briefly stated the coated substrate whether small bodies or on a plate bearing the first partner, will have applied to it a known quantity (sample) of test serum containing the second partner (occasionally also a third partner) being assayed inn a suitable buffer solution. The presence or absence, and if present the concentration of this second or third partner is determined by a subsequent procedure.

In addition there will be added a known amount of the same second or third partner for which the assay is intended. However, this additional second or third partner is "marked" (the sample partner is not marked). For fluoroscopic assays, it is dyed with a fluorescent dye. This is the arrangement for "competitive" type assays. For Raman-type assays, the additional second partner is supplied with a Raman tag.

In both cases, the sample second partner and added second partner tend to bond to the first partner on the microspheres or on a plate. The bonding mechanisms are not of concern to this invention—they are generally known and are conventional.

After a suitable period of incubation, generally between about 5 and about 180 minutes, the consumable will be exposed to appropriate radiation and the emissions will be measured.

In the fluoroscopic assay, the bound material fluoresces more vigorously than the unbound. Alternately the consumable can be bleached out, and it can be observed that the bound material continues to respond. In either event, the fluorescence is significantly increased by the presence and correct dimensions of the silver islands and of the coupling layer.

With Raman-type assays, the emissions from the bound material are more vigorous than of the unbound material because of the precise spacing of the silver from the Raman tag. This appears to yield a much stronger signal. In selecting the thickness; of the coupling agent layer it will be noted that Raman type assays best utilize thinner layers, and fluorescent and colorimetric type assays tend to use thicker layers.

The following are lists of partners which can be utilized in pairs, or in some analyses, three partners. Speaking generally partner A will usually be the partner supplied on the consumable, while partner B and/or partner C will generally (but not always) be the subject of the analysis, and will be applied to the consumable during the analytical procedure.

Partner A any antibody any hapten any derivatized hapten any nucleic acid antigen any lipid any polysaccharide any nucleotide any protein antigen protein A protein G any cellular antigen in tissue any aromatic or organic compound

Partner B specific binding partners to any of partners A, further including but not limited to an organic derivative a biotinylated antibody streptavidin avidin and any of the above labelled with a Raman tag, or with a fluorescent or colorimetric dye

Partner C specific binding partners to any of partners B, labelled with a Raman tag or with a fluorescent or colorimetric dye, the partner B not being labelled.

It will be observed that many of the partners can be used as first, second or third partners. Their characterization is not intended to reduce the scope of their utility. Instead, the term first partner is used to denote the partner which will be applied to, or be imbued within, the coupling layer. The second partner is the partner added during the analytical procedure, usually as a sample and as a marked or tagged moiety as well. Partner C denotes the partner which couples with the second partner, to be sensed or measured after the second partner has coupled with the first partner. Thus, partner C, which is in effect a third partner, is coupled the first partner A through a second partner B, which acts as an intermediary.

Examples of well-known suitable first partners are rabbit IgG, goat IgG, and mouse IgG, and can be monoclonal in nature. These are antibodies which normally exhibit high specificity and good kinetic binding characteristics.

Examples of well-known second and third partners are antigens that can be assayed with the consumable of this invention are: lipopolysaccharides; proteins such as vital proteins, human proteins and tumor markers; complex carbohydrates such as glucagon and insulin; and aromatic hydrocarbons such as are found in air pollutants.

Stated generally, the foregoing lists, which are not exclusive of other analagous substances, represent a broad range of utility which will serve laboratories well. They provide consumables with measurable and known quantities of partners with which other partners can be used to carry out an analysis. In summary it is emphasized that this invention does not reside in any particular immunoassay technique. These are known art. Neither does it reside in the use of silver islands, which also is known. Also, at least as to fluorescent techniques, it is known that the thickness of a coating on a substrate having silver islands can have an effect on the enhancement factor of a fluorescent dye, but no use was made of this for assay purposes.

What has not previously been known, and is submitted to be the essence of this invention, is that by the use of the combination of a substrate with metal island on it and a coupling agent on it of known thickness, and a first partner on the surface of the coupling agent, then an analytical procedure can be made which is remarkably faster and more sensitive than known procedures.

This invention thereby provides a consumable having a surface which bears a partner useful in analytical procedures. The sensitivity of the process is greatly increased by virtue of the small metal islands, and the spacing of the partner from the metal island by a layer of coupling agent.

This invention is not to be limited to the embodiments shown in the drawings and described in the description which are given by way of example and not of limitation, but only in accordance with the scope of the appended claims.

I claim:

1. A process for forming a surfaced article for a surface-enhanced analytical procedure comprising the following steps in the order recited:
    a. providing a bead substrate body having a substrate surface;
    b. applying to said substrate surface a population of spaced apart metal islands, on and adherent to said substrate surface;
    c. forming interconnections between at least some of the metal islands, the interconnections being metal and of lesser thickness than the metal islands;
    d. coating said metal islands and all surfaces between them with a continuous layer of coupling agent, said coupling agent having the capacity to adhere to the metal islands and to the surfaces between them, and to be bondable to first partner molecules;
    e. applying to said coupling agent layer the first binding partner molecules, the first binding partner molecules selected for having a specific binding affinity to specific second binding partner molecules, the second binding partner molecules not bonded to the coupling agent layer, wherein said second binding partner molecules are a reagent in said specific surface-enhanced analytical procedure, and
    f. bonding said second binding partner molecules to the first binding partner molecules.

2. A surfaced article for use in a specific surface-enhanced analytical procedure for detecting or measuring the concentration of a specific third binding partner molecule, said article comprising:
    a bead substrate body having a non-metallic substrate surface;
    a population of randomly spaced apart metal islands on said substrate surface, said metal being selected from the group consisting of silver, gold, platinum, copper, nickel, indium and germanium;
    interconnections between at least some of the metal islands, the interconnections being metal and of lesser thickness than the metal islands;
    a continuous layer of coupling agent coating said islands and also coating all surfaces between them which were exposed before the coupling agent was applied, said coupling agent having the capacity to adhere to the metal and to the substrate where exposed, and to be bondable to first binding partner molecules, said islands before being coated with said coupling agent having an exposed surface, said islands and exposed surfaces forming a roughened surface which is coated with said coupling agent;
    first binding partner molecules being bonded to said coupling agent layer and having binding affinity for second binding partner molecules; and
    second binding partner molecules bonded to said first binding partner molecules, wherein said second binding partner molecules have specific binding affinity for said third binding partner molecules.

3. A surfaced article according to claim 2 in which said coupling agent is selected from the group consisting of polyglutaraldehyde (PEA), protein A, protein G, polystyrenes, polyethylenes, polyacrylamides, streptavidin, avidin, slices of tissue, cellulosic materials, foams and sponges.

4. A surfaced article according to claim 3 in which the lateral dimensions of the substrate body are generally between about 25 nm to 10 microns.

5. A surfaced article according to claim 2 in which the lateral dimensions of the substrate body are generally between about 25 nm to 10 microns.

6. A surfaced article according to claim 5 in which the substrate body is bounded by a closed surface.

7. A surfaced article according to claim 6 in which said metal islands have nominal dimensions within the range defined by the following equation:

$$\frac{\text{Metal Thickness}}{\text{Metal Thickness} + \text{Diameter of the substrate body}} = \text{about } 0.58 \text{ to about } 0.67.$$

8. A surfaced article according to claim 2 in which said substrate material is selected from the group consisting of polystyrene, glass, latex, polyethylene, nylon, polypropylene, silicone rubber, silica, and ceramic.

9. A surfaced article according to claim 2 in which the thickness of the silver islands is on the order of 20 to 200 Angstroms.

10. A surfaced article according to claim 2 in which the lateral dimensions of the substrate body are generally between about 25 nm to 10 microns.

11. A surfaced article according to claim 2 in which the height of the silver islands above said deposits of lesser thickness is on the order of about 20 to about 200 Angstroms.

12. A surfaced article according to claim 2 in which one of said binding partners is an antibody.

13. A reagent for a surface-enhanced analytical procedure comprising a plurality of surfaced articles according to claim 2.

14. A process for forming a surfaced article for a specific surface-enhanced analytical procedure comprising the following steps in the order recited:
    a. providing a bead substrate body having a substrate surface;

b. applying to said substrate surface a population of spaced apart metal islands, on and adherent to said substrate surface;

c. forming interconnections between at least some of the metal islands, the interconnections being metal and of lesser thickness than the metal islands;

d. coating said metal islands and all surfaces between them with a continuous layer of coupling agent, said coupling agent having the capacity to adhere to the metal islands and to the surfaces between them, and to be bondable to first partner molecules, said islands before being coated with said coupling agent having an exposed surface which with said exposed surfaces between them, form a roughened surface which is coated with said coupling agent;

e. applying to said coupling agent layer the first binding partner molecules, the first binding partner molecules selected for having a specific binding affinity to specific second binding partner molecules, the second binding partner molecules not bonded to the coupling agent layer, wherein said second binding partner molecules are a reagent a reagent in said specific surface-enhanced analytical procedure; and f. bonding said second binding partner molecules to the first binding partner molecules.

15. A surfaced article for use in a surfaced-enhanced, analytical procedure, comprising:

a substrate body having a substrate surface, the substrate body being a bead;

a population of spaced apart metal islands on said substrate surface, said metal being selected from the group consisting of silver, gold, platinum, copper, nickel, indium and germanium;

interconnections being formed between at least some of the metal islands, the interconnections being metal and of lesser thickness than the metal islands;

a continuous layer of a coupling agent coating said islands, and also coating all surfaces between the metal islands which are exposed before the coupling agent was applied, said coupling agent having the capacity to adhere to the metal and to the substrate where exposed;

first binding partner molecules bonded to said coupling agent layer; and second binding partner molecules bonded to said first binding partner molecules not bonded to the coupling agent layer, the first binding partner molecules being binding partners of the second binding partner molecules, said first and second partner molecules being different molecules having specific binding affinity for each another.

16. A surfaced article according to claim 15 in which said coupling agent is selected from the group consisting of polyglutaraldehyde (PGA), protein A, protein G, polystyrenes, polyethylenes, polyacrylamides, streptavidin, avidin, slices of tissue, cellulosic materials, foams and sponges.

17. A surfaced article according to claim 16 in which the lateral dimensions of the substrate body are generally between about 25 nm to 10 microns.

18. A surfaced article according to claim 15 in which the lateral dimensions of the substrate body are generally between about 25 nm to 10 microns.

19. A surfaced article according to claim 18 in which the substrate body is bounded by closed surface.

20. A surfaced article according to claim 19 in which said metal islands have nominal dimensions within the range defined by the following equation:

$$\frac{\text{Metal Thickness}}{\text{Metal thickness} + \text{Diameter of the substrate body}} = \text{about } 0.58 \text{ to about } 0.67.$$

21. A surfaced article according to claim 15 in which said substrate material is selected from the group consisting of polystyrene, glass, latex, polyethylene, nylon, polypropylene, silicone rubber, silica, and ceramic.

22. A surfaced article according to claim 15 in which the thickness of the silver islands is on the order of 20 to 200 Angstroms.

23. A surfaced article according to claim 15 in which the thickness of the coupling agent coating is about 5 Angstroms to about 10 microns.

24. A surfaced article according to claim 15 in which the height of the silver islands above said deposits of lesser thickness is on the order of about 20 to about 200 Angstroms.

25. A surfaced article according to claim 15 in which one of said binding partners is an antibody.

26. A reagent for an immunoassay procedure comprising a plurality of surfaced articles according to claim 15.

* * * * *